United States Patent [19]

Paterson

[11] Patent Number: 5,512,213
[45] Date of Patent: Apr. 30, 1996

[54] AQUEOUS STABILIZED ISOTHIAZOLONE BLENDS

[75] Inventor: Donald J. Paterson, Jacksonville, Fla.

[73] Assignee: Betz Laboratories, Inc., Trevose, Pa.

[21] Appl. No.: 396,940

[22] Filed: Mar. 1, 1995

[51] Int. Cl.$^6$ .................. A01N 59/00; A01N 43/80; C07D 275/03
[52] U.S. Cl. ............ 252/400.62; 548/213; 514/372; 252/400.2; 252/400.1; 252/400.4; 252/405; 252/406; 252/407; 424/666; 424/722; 424/601; 424/602
[58] Field of Search ............... 548/213; 514/372; 252/400.62; 424/666

[56] References Cited

U.S. PATENT DOCUMENTS

| | | | |
|---|---|---|---|
| 3,870,795 | 3/1975 | Miller et al. | 424/270 |
| 4,067,878 | 1/1978 | Miller et al. | 260/302 A |
| 4,150,026 | 4/1979 | Miller et al. | 260/299 |
| 4,396,413 | 8/1983 | Miller et al. | 71/67 |

FOREIGN PATENT DOCUMENTS

| | | |
|---|---|---|
| 2027241 | 10/1990 | Canada . |
| 2029562 | 11/1990 | Canada . |

OTHER PUBLICATIONS

Chemical Abstracts 120(11), Abstract No. 127766f, (1994).

*Primary Examiner*—Johann Richter
*Assistant Examiner*—Laura R. Cross
*Attorney, Agent, or Firm*—Alexander D. Ricci; Richard A. Paikoff

[57] ABSTRACT

A treatment for stabilizing an isothiazolone compound comprising adding to the compound a stabilizing amount of a metal salt, wherein the cation of the metal salt is an alkali metal, and the anion is selected from the group consisting of acetate, citrate, phosphate and borate.

11 Claims, No Drawings

AQUEOUS STABILIZED ISOTHIAZOLONE BLENDS

BACKGROUND OF THE INVENTION

The use of 3-isothiazolones to control microbial growth in a variety of industrial environments (metal working fluids, cooling tower water, emulsions, plastic film, and the like) has been enhanced by the addition of stabilizers to maintain antimicrobial activity for longer periods of time; typical stabilizer systems include metal nitrates and the like.

U.S. Pat. Nos. 3,870,795 and 4,067,878 teach the stabilization of isothiazolones against chemical decomposition by addition of a metal nitrite or metal nitrate salts, but teach that other common metal salts, including carbonates, sulfates, chlorates, perchlorates, and chlorides are not as effective as nitrates or nitrites in stabilizing solutions of isothiazolones, such solutions usually being in water or in an hydroxylic solvent and immiscible with solvent-soluble isothiazolones.

Formaldehyde or formaldehyde-releasing chemicals are known stabilizers. In certain applications, however, it is desirable to avoid addition of organic stabilizers by virtue of their volatility, decomposition under high heat, higher costs, difficulty in handling, potential toxicity, and the like.

The use of copper as a stabilizer poses two significant problems. Restrictive environmental regulations prohibit the direct discharge of heavy metal salts. This is related to the toxicity of copper ions. These restrictions reduce the use of this biocide (i.e., isothiazolone) in cooling tower applications. Copper also increases the potential for corrosion problems. The use of copper containing biocides must be continually monitored.

The use of ferric chloride to stabilize isothiazolone solutions suffers from a very low pH. This pH range places the product in a hazardous and corrosive category. The presence of iron salts also limits application in paper systems due to concerns regarding brightness reversion of bleached paper.

The present invention eliminates the need for the use of certain metal salts to stabilize the isothiazolone. The potential corrosion problems and known toxicity of some metal salts are thus overcome.

DESCRIPTION OF THE PREFERRED EMBODIMENTS

The present invention comprises a composition comprising (a) a 3-isothiazolone compound of the formula:

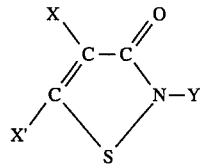

wherein Y is an alkyl or substituted alkyl of 1 to 18 carbon atoms; an unsubstituted or halogen substituted alkenyl or alkynyl of about 2 to 8 carbon atoms; a cycloalkyl or substituted cycloalkyl of about 3 to 12 carbon atoms; an aralkyl or halogen-, lower alkyl-, or lower alkoxy-substituted aralkyl of up to about 10 carbon atoms; or an aryl or halogen-, lower alkyl-, or lower alkoxy-substituted aryl of up to about 10 carbon atoms; and X and X' are hydrogen, halogen, or a ($C_1$–$C_4$) alkyl; and (b) a stabilizing amount of a metal salt, where the cation of the metal salt is an alkali metal (e.g., sodium, potassium), and the anion is selected from the group consisting of acetate, citrate, phosphate and borate.

Representative Y substituents include methyl, ethyl, propyl, isopropyl, butyl, hexyl, octyl, cyclohexyl, benzyl, 3, 4-dichlorophenyl, 4-methoxybenzyl, 4-methoxybenzyl, 4-chlorobenzyl, 3, 4-dichlorophenyl, 4-methoxyphenyl, 4-chlorophenyl, phenethyl, 2-(4-chlorophenyl)ethyl, hydroxymethyl, chloromethyl, chloropropyl, hydrogen, and the like.

Where the expression "lower" is employed in conjunction with terms, such as alkyl, alkoxy, etc., it is intended to indicate that the alkyl or alkyl portion thereof has from about 1 to 4 carbon atoms.

By a substituted alkyl group it is meant an alkyl group having one or more of its hydrogen atoms replaced by another substituted group. Examples of these substituted alkyl groups which characterize 3-isothiazolones of this invention include hydroxyalkyl, haloalkyl, cyanoalkyl, alkylaminoalkyl, dialkylaminoalkyl, aryl aminoalkyl, carboxyalkyl, carbalkoxyalkyl, alkoxyalkyl, aryloxyalkyl, alkylthioalkyl, arylthioalkyl, haloalkoxyalkyl, cycloalkylaminoalkyl, such as morpholinoalkyl, piperidinoalkyl, pyrrolidonylalkyl, and the like, carbamoxyalkyl, alkenyl, haloalkenyl, alkynyl, haloalkynyl, isothiazolonylalkyl and the like.

By a substituted aralkyl group it is meant an aralkyl group having one or more of the hydrogen atoms on either the aryl ring or the alkyl chain replaced by another substituent group. Examples of the substituent aralkyl groups which characterize 3-isothiazolones of this invention include halogen-, lower alkyl-, or lower alkoxy-substituted aralkyl groups, and the like. By a substituted aryl group it is meant an aryl group, such as benzene, naphthalene, or pyridine, having one or more of the hydrogen atoms on the aryl ring replaced by another substituent group. Examples of such substituent group include halogen, nitro, lower alkyl, lower alkylacrylamino, lower carbalkoxy, sulfamyl and the like.

Preferred isothiazolones are 5-chloro-2-methyl-3-isothiazolone, 2-methyl-3-isothiazolone, 2-n-octyl-3-isothiazolone, and 4, 5-dichloro-2-octyl-3-isothiazolone.

Among the stabilizing solutions useful in the compositions of the present invention are mixtures of sodium acetate and acetic acid, mixtures of sodium citrate and hydrochloric acid, and mixtures of phosphoric, boric and acetic acids.

The amounts of stabilizing buffer solution employed will vary depending on use conditions and concentrations of the isothiazolone in the mixture. In more concentrated solutions, effective amounts of buffer solution are from about 0.02 molar to about 2.0 molar, with about 0.2 molar preferred.

The following examples will further illustrate the present invention, but are not intended to limit it in any way. All parts and percentages are by weight, unless otherwise stated. The particular isothiazolone tested is a mixture of 5-chloro-2-methyl-3-isothiazolone and 2-methyl-3-isothiazolone (assay) in about a 3:1 weight ratio of each.

EXAMPLES

The following examples demonstrate that degradation of isothiazolone may be minimized through control of pH by using buffers. Tables I through IV below show the effects of several buffer solutions at various buffer solution pH values (pHo) on the chemical stability of isothiazolone after storage at 50° C. for 4 and 8 weeks.

TABLE I

Sodium Acetate-Acetic Acid Buffer System
Buffer pHo, Blend pHi and Chemical Assay
vs. Storage Time at 50° C.

| Sample | Buffer pHo | Assay t(o) | Assay t(4w) | Assay t(8w) | Active Remaining 4w | 8w |
|---|---|---|---|---|---|---|
| 1 | 3.77 | 3.9 | 3.8 | 3.3 | 97% | 85% |
| 2 | 3.99 | 3.9 | 3.9 | 3.7 | 100% | 95% |
| 3 | 4.30 | 3.9 | 3.8 | 3.8 | 97% | 97% |
| 4 | 4.79 | 3.9 | 3.8 | 3.7 | 97% | 95% |
| 5 | 5.19 | 3.9 | 3.7 | 3.6 | 95% | 92% |
| 6 | 5.56 | 3.9 | 3.6 | 3.2 | 92% | 82% |
| 7 | 5.75 | 3.9 | 3.5 | 3.0 | 90% | 77% |

TABLE II

Sodium Citrate-Hydrochloric Acid Buffer System
Buffer pHo, Blend pHi and Chemical Stability
vs. Storage Time at 50° C.

| Sample | Buffer pHo | Assay t(o) | Assay t(4w) | Assay t(8w) | Active Remaining 4w | 8w |
|---|---|---|---|---|---|---|
| 1 | 3.75 | 3.9 | 3.7 | 3.4 | 95% | 87% |
| 2 | 3.81 | 3.9 | 3.8 | 3.5 | 97% | 90% |
| 3 | 3.90 | 3.9 | 3.8 | 3.4 | 97% | 87% |
| 4 | 3.93 | 3.9 | 3.8 | 3.7 | 97% | 95% |
| 5 | 4.09 | 3.9 | 3.8 | 3.6 | 97% | 92% |
| 6 | 4.14 | 3.9 | 3.8 | 3.7 | 97% | 95% |
| 7 | 4.29 | 3.9 | 3.8 | 3.8 | 97% | 97% |
| 8 | 4.45 | 3.9 | 3.8 | 3.7 | 97% | 95% |
| 9 | 4.66 | 3.9 | 3.9 | 3.2 | 100% | 82% |
| 10 | 4.94 | 3.9 | 3.8 | 3.6 | 97% | 92% |

TABLE III

Mixed Acid Control Buffer System of
Phosphoric, Boric and Acetic Acids with NaOH
Buffer pHo, Blend pHi and Chemical Assay
vs. Storage Time at 50° C.

| Sample | Buffer pHo | Assay t(o) | Assay t(4w) | Assay t(8w) | Active Remaining 4w | 8w |
|---|---|---|---|---|---|---|
| 1 | 3.08 | 3.9 | 3.5 | 2.8 | 90% | 72% |
| 2 | 3.61 | 3.9 | 3.6 | 2.8 | 92% | 72% |
| 3 | 3.86 | 3.9 | 3.9 | 2.9 | 100% | 74% |
| 4 | 4.40 | 3.9 | 3.9 | 3.3 | 100% | 85% |
| 5 | 4.62 | 3.9 | 3.9 | 3.6 | 100% | 92% |
| 6 | 4.67 | 3.9 | 3.8 | 3.5 | 97% | 90% |
| 7 | 5.27 | 3.9 | 3.9 | 3.8 | 100% | 97% |
| 8 | 5.51 | 3.9 | 3.8 | 3.8 | 97% | 97% |
| 9 | 5.77 | 3.9 | 3.8 | 3.7 | 97% | 95% |
| 10 | 5.82 | 3.9 | 3.8 | 3.7 | 97% | 95% |

TABLE IV

Sodium Phosphate Dibasic-Citric Acid Buffer System
Buffer pHo, Blend pHi and Chemical Assay
vs. Storage Time at 50° C.

| Sample | Buffer pHo | Assay t(o) | Assay t(4w) | Assay t(8w) | Active Remaining 4w | 8w |
|---|---|---|---|---|---|---|
| 1 | 2.74 | 3.9 | 3.0 | 2.1 | 77% | 54% |
| 2 | 2.81 | 3.9 | 3.0 | 2.4 | 77% | 62% |
| 3 | 3.41 | 3.9 | 3.1 | 2.3 | 79% | 59% |
| 4 | 3.61 | 3.9 | 3.4 | 2.5 | 87% | 64% |
| 5 | 3.91 | 3.9 | 3.7 | 3.1 | 95% | 79% |
| 6 | 4.30 | 3.9 | 3.8 | 1.8 | 97% | 46% |
| 7 | 4.99 | 3.9 | 3.8 | 3.5 | 97% | 90% |
| 8 | 5.39 | 3.9 | 3.8 | 3.4 | 97% | 87% |
| 9 | 5.70 | 3.9 | 3.8 | 3.7 | 97% | 95% |
| 10 | 5.99 | 4.0 | 3.8 | 3.5 | 97% | 90% |

Tables I through IV show that there is a range of buffer solution pH (pHo) of between about 3.7 and 5.2 where the isothiazolinone loss is less than or equal to 8% over a 4 week period, based on the initial assay. The pHo range for isothiazolinone stability becomes smaller for longer storage times at 50° C., and is more specific to the type of buffer system. For example, the pHo range for 8 week stability of the acetic acid-sodium acetate buffer system is unchanged. The pHo range for 8 week stability of the phosphoric, boric, acetic acids and sodium hydroxide buffer system is between 5.3 and 5.8.

Note that other buffer systems, such as succinic acid/sodium borate, or hydrochloric acid/glycine, are also expected to be effective.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

I claim:

1. A method of stabilizing an aqueous solution containing an isothiazolone compound against chemical decomposition of the compound which comprises adding to the solution a stabilizing amount of a metal salt, wherein the cation of said metal salt is an alkali metal, and the anion is selected from the group consisting of acetate, citrate, phosphate and borate.

2. The method as recited in claim 1 wherein said alkali metal is sodium.

3. The method as recited in claim 1 wherein said alkali metal is potassium.

4. The method as recited in claim 1 wherein the metal salt is combined with an acid in the form of a buffer solution.

5. The method as recited in claim 4 wherein the buffer solution is a mixture of sodium acetate and acetic acid.

6. The method as recited in claim 4 wherein the buffer solution is a mixture of sodium citrate and hydrochloric acid.

7. The method as recited in claim 1 wherein the isothiazolone compound is selected from the group consisting of 5-chloro-2-methyl-3-isothiazolone, 2-methyl-3-isothiazolone, 2-n-octyl-3-isothiazolone, and 4,5-dichloro-2-octyl-3-isothiazoione.

8. The method as recited in claim 4 wherein the concentration of the buffer solution is from about 0.02–2.0 molar.

9. A composition comprising an isothiazolone compound and a stabilizing amount of a metal salt combined with an acid in the form of a buffer solution, wherein the cation of said metal salt is an alkali metal, and the anion is selected from the group consisting of acetate, citrate, phosphate and borate.

10. The composition as recited in claim 9 wherein said buffer solution is a mixture of sodium acetate and acetic acid.

11. The composition as recited in claim 9 wherein said buffer solution is a mixture of sodium citrate and hydrochloric acid.

* * * * *